United States Patent [19]

Shibata et al.

[11] Patent Number: 4,836,987

[45] Date of Patent: Jun. 6, 1989

[54] TEST TUBE ASSEMBLY FOR SERUM SEPARATION

[75] Inventors: Toshiko Shibata, Ichikawa; Hiroji Ina, Tama; Kazuo Ina, Shizuoka, all of Japan

[73] Assignee: Nippon Paint Co., Ltd., Japan

[21] Appl. No.: 242,115

[22] Filed: Sep. 8, 1988

Related U.S. Application Data

[62] Division of Ser. No. 841,096, Mar. 18, 1986, Pat. No. 4,803,153.

[30] Foreign Application Priority Data

Mar. 19, 1985 [JP] Japan .................................. 60-053328

[51] Int. Cl.$^4$ ......................... B01L 11/00; A01N 1/02; C12Q 1/56
[52] U.S. Cl. ..................................... 422/101; 422/56; 422/57; 422/58; 435/2; 435/13; 210/730
[58] Field of Search ............................ 422/101, 56–58; 435/2, 13; 210/730

[56] References Cited

U.S. PATENT DOCUMENTS

| 4,140,631 | 2/1979 | Okuda et al. | 210/83 |
|-----------|--------|--------------|--------|
| 4,295,974 | 10/1981 | Cornell | 422/101 |
| 4,426,290 | 1/1984 | Ichikawa et al. | 422/101 |
| 4,427,694 | 1/1984 | Benecke et al. | 424/282 |
| 4,440,789 | 4/1984 | Mattei et al. | 424/78 |
| 4,539,332 | 9/1985 | Biftu et al. | 514/461 |

OTHER PUBLICATIONS

Beroza et al, *Journal of the American Chemical Society*, vol. 78, pp. 1242–1247 (1956).

*Primary Examiner*—Johnnie R. Brown
*Assistant Examiner*—Jacqueline M. Stone
*Attorney, Agent, or Firm*—Lowe, Price, LeBlanc, Becker & Shur

[57] ABSTRACT

A coagulant or hemostatic comprises, as an effective ingredient, at least one compound consisting of a lignan skelton having oxygen-containing side chains or rings.

8 Claims, No Drawings

TEST TUBE ASSEMBLY FOR SERUM SEPARATION

This is a division, of application Ser. No. 841,096, filed 3/18/86 now U.S. Pat. No. 4,803,153.

BACKGROUND OF THE INVENTION

1. Field of the Invention

This invention concerns active substances to promote the coagulation of blood sampled for examination and, more particularly, it relates to coagulants which are used for separating serum or plasma (hereinafter referred to as serum) from the whole blood for testing the serum in a shorter time and at a higher yield and for use in hemostasis.

2. Description of the Prior Art

With the increase in the number of blood specimens to be examined, various studies have been made and put to practical use for improving the efficiency of separating serum from blood. Since the serum is mostly examined in the blood test, it is desirable to separate the serum from the whole blood with no contaminations in a short time and at a high yield. For the purpose of separation, it has been recognized as effective to use a so-called serum separating sealant of a high molecular substance for forming partitions such as silicones, or polyether resins and acryl resins as disclosed in U.S. Pat. No. 4,140,631 having an intermediate specific gravity between the liquid serum portion and the solid corpuscular portion (hereinafter referred to as a separating gel), as well as a blood coagulant in combination.

With the reason as described above, means for promoting blood coagulation are used for attaining the separation of the serum from the whole blood in a short time at a high accuracy. As the agents to be used for promoting blood coagulation, there have been reported, for instance, finely powderous or fibrous silicate compounds such as kaolin, Celite, diatomaceous silica and glass fibers, fine powders of calcium compounds such as calcium carbonate and calcium sulfate, thrombin-like substances derived from snake venoms, and polyphenols that can activate blood clotting factors to promote the coagulation. Further, there have been reported various methods of using these substances, for example, adding one or more of them into a blood to be separated, coating them to the inside wall of a serum separation test tube, coating or depositing them onto an appropriate carrier which is then placed in the test tube, or dispersing them in the separating gel.

However, if the coagulant is dispersed into the separating gel, no satisfactory effect of promoting the coagulation can be obtained because of reduction in the contact between the coagulant and the blood and hemolysis may sometimes be caused during centifugal separation of the blood.

Coagulants derived from snake venoms involve problems in that they are effective only for a short period of time and are expensive as well. Other coagulants may also cause problems in that the coagulation time can not be shortened as expected, and impurities are introduced into the serum.

SUMMARY OF THE INVENTION

The object of this invention is to overcome the foregoing problems in the prior art and provide a coagulant capable of promoting the blood coagulation without developing hemolysis and thereby rapidly separating the serum with no undesired effects on the measured values of various test parameters.

The object of this invention has been achieved according to this invention with a compound consisting of a lignan skelton having an oxygen-containing side chains or rings. Specifically, this invention provides a coagulant or hemostatic comprising, as an effective ingredient, at least one compound consisting of a lignan skelton having an oxygen-containing side chains or rings.

DETAILED DESCRIPTION OF THE INVENTION

Examples of Effective Compound

Compounds consisting of a lignan skelton having an oxygen-containing side chains or oxygen-containing rings are present in the fraction obtained from extracts from certain kinds of plants of umballiferas and aristolochiaceae.

Specific examples of the compounds having the foregoing chemical structure and used as coagulants are those as shown below: d-sesamin, l-sesamin, paulownin, d-asarinin, l-asarinin, $2\alpha$-paulownin, $6\alpha$-paulownin, pinoresinol, d-eudesmin, l-pinoresinol $\beta$-D-glucoside, l-pinoresinol, l-pinoresinol monomethyl ether $\beta$-D-glucoside, epimagnolin, lirioresinol-B, syringaresinol (dl), lirioresinon-B-dimethyl ether, phillyrin, magnolin, lirioresinol-A, $2\alpha,6\alpha$-d-sesamin, d-diaeudesmin, lirioresinol-C dimethyl ether (d-diayangambin) and sesamolin.

All of the above-mentioned compounds, as well as natural substances, plant cultured products and synthetic substances having chemical structures similar to these compounds have coagulation promoting effects.

MODE OF USE

The coagulants according to this invention may be added in the form of powder or aqueous suspension to a sample to be tested composed of a blood. Alternatively, the coagulants according to this invention dissolved or dispersed into a suitable solvent or binder may be applied to the inside wall of a serum separation test tube, or they may be coated on those carriers such as glass beads or glass fibers inactive to the blood and capable of supporting them and then placed in a test tube.

The coagulants according to this invention can be used with sufficient effect as an active ingredient in an amount ranging from 0.01 to 50 mg, preferably, from 0.1 to 20 mg per 1 ml of the blood. Further, the effect of the coagulants according to this invention can be enhanced by the combined use with known blood coagulating substances such as powdered silica, kaolin, glass, or fiberous glass materials.

ADVANTAGE OF THE INVENTION

The coagulants according to this invention can accelerate the blood coagulation time and the progress in clot retraction, leave no fibrin in the serum and cause no hemolysis (that is, contributing to the improvement in the yield of the serum and the accuracy in the clinical examination).

Besides, the serum obtained by the treatment and separation with the chemicals of this invention gives no adverse effects on biochemical and immunochemical examination.

Furthermore, since the chemicals according to this invention have a nature of coagulating the blood, they can also be applied as hemostatics. Furthermore, sesamin can be used as a psychotropic agent and natural lignan (sesamin and asarinin, etc.) has tuberculostatic and anti-cancer effects.

EMBODIMENT OF THE INVENTION

This invention will be more fully described by way of the following examples, but is not limited only thereto.

EXAMPLE 1

*Hydrocotyle sibthorpioides* was subjected to extraction to obtain an active fraction by the following procedures:

The whole of the dried grass of 600 g was subjected to extraction three times each with 3 liters of methanol, and then the extract was concentrated to make 100 ml of methanol extract. To the extract, an equal amount of water was added, which was divided into soluble and insoluble parts. 16.5 g of the insoluble part was subjected to extraction with 1 liter of benzene and the benzene was evaporated to obtain 16 g of a benzene extract (viscous substance) and a residue. 16 g of the benzene extract was purified on column chromatography and it was found that the purified substance was composed of l-sesamin having molecular weight of 354, melting point at 122°–123° C. and $[\alpha]_D^{18} = -64.5°$.

EXAMPLE 2

*Asiasarum sieboldi* was subjected to extraction to obtain an active fraction by the following procedures:

500 g of dried tubers of *Asiasarum sieboldi* were subjected to extraction three times each with 3 liters of methanol and then concentrated to obtain 34 g of methanol extract. 100 ml of 50% aqueous solution of sodium hydroxide were added and shaken, followed by extraction with 500 ml of ethyl ether. The extract was concentrated to obtain 35 g of ether extract, which was found to be an active fraction composed of l-asarinin and l-sesamin as the main ingredient based on the following analytical values.

| | |
|---|---|
| l-asarinin: | molecular weight: 354, melting point: 122° C. $[\alpha]_D^{18} = -118°$ |
| l-sesamin: | molecular weight: 354, melting point: 122 – 123° C.: $[\alpha]_D^{18} = -63.5°$ C. |

EXAMPLE 3

Sodium ethyl acetate (NaCH(COCH$_3$).COOC$_2$H$_5$) in an amount of 20 g was added to 12 g of piperonyl chloride and the mixture thus obtained was heated to reflux in 300 ml of ethyl ether, followed by concentration to obtain ethyl piperonyl acetate. Then, 50 ml of 1% aqueous ammonia and 5 g of ammonium chloride powder were added to the resultant concentrate and the obtained mixture was heated to reflux, followed by concentration to obtain ethylpiperonyl acetate. Then, 25 ml of 3% ethanol solution of sodium and 50 ml of 9% ether solution of iodine were added to the ethylpiperonyl acetate to obtain diethyl 2,3-bis(3,4-methylenedioxybenzoyl)succinate. The succinate was refluxed in a 70 ml of 1.6% ether solution of lithium aluminum hydride to obtain 1,4-bis-(3,4-methylene-dioxyphenyl-2,3-bishydroxymethyl)-1,4-butandiol. Then, 7 ml of concentrated hydrochloric acid and 50 ml of ethanol were added, stirred at room temperature and then refluxed. After being left at room temperature, it was found that the substance was the aimed active substance, d-sesamin, since it had molecular weight of 354; melting point at 125°–126° C.

Activity Test Example 1a and 1b

The active substance containing l-sesamin as the main ingredient obtained in Example 1 was dissolved by an amount of 50 mg in 10 ml of a 1:1 mixed solution of methylene chloride and chloroform, and the resulted solution was applied to the inside of a glass test tube "a" or a plastic test tube "b" for use a in blood test (both "a" and "b" were 13 mm in inner diameter and 10 ml in volume), which had been filled with a serum separating gel, to a level from 30 to 35 mm from the top of the separating gel. Then, the solvent was completely evaporated in a drying oven to prepare a test tube on which the active substance was coated by an amount from 5 to 7 mg. After pouring 6 ml of fresh human blood into the test tube, the test tube was left in a thermostable chamber at a temperature of 20° C. Then, the blood coagulation time was determined as the time taken until the blood could flow no more if the test tube was slanted by 90°. Then, the serum separated by centrifugation at 1600 G×5 min. on the separating gel was collected by decantation and the amount was measured. The degree of the hemolysis was judged with the naked eye based on the evaluation criteria shown in Table 2. The results are shown in Table 1. In Table 1, the results for the test using the glass test tube are shown as Test Example a and those using the plastic test tube are shown as Test Example b.

When carrying out biochemical and immunochemical examinations on the serum separated from the blood by using the active substance obtained in Example 1, no undesired effects were recognized on the test values.

Active Test Examples 2a and 2b

Measurements and evaluation were carried out by the same procedures as in Test Examples 1a and 1b, except for using the active substance mainly composed of l-asarinin obtained in Example 2. The results are shown in Table 1.

When carrying out biochemical and immunochemical examinations on the serum separated from the blood by using the active substance obtained in Example 2, no undesired effects were recognized on the test values.

Active Test Examples 3a and 3b

Measurements and evaluation were carried out by the same procedures as in Test Examples 1a and 1b, except for using the active substance mainly composed of l-asarinin obtained in Example 3. The results are shown in Table 1. The results for the test using the substance coated on the glass test tube are shown the Test Example "a" and those using the substance coated on the plastic test tube are shown as Test Example "b".

When carrying out biochemical and immunochemical examinations on the serum separated from the blood by using the active substance obtained in Example 3, no undesired effects were recognized on the test values.

Comparative Examples 1a and 1b

The same type of glass and plastic blood-examination test tubes as used in Examples 3 were filled with the serum separating gel, and the coagulation of blood, serum yield and hemolysis were measured and evaluated under the same conditions as in Test Example 1. The results are shown in Table 1.

Comparative Example 2

A blood sampling glass tube available on the market filled with a separating gel and applied with an inorganic fine powder at the inside wall thereof was used for the measurement and evaluation under the same procedures as in Test Example 1. The results are shown in Table 1.

TABLE 1

| | Coagulation promoting effect | | |
|---|---|---|---|
| | Coagulation time (min) | Volume of serum (ml) | Nemolysis |
| Test Example | | | |
| 1a | 17 | 3.0 | — |
| 1b | 21 | 3.0 | — |
| 2a | 19 | 3.0 | — |
| 2b | 24 | 2.7 | ± |
| 3a | 20 | 2.9 | — |
| 3b | 27 | 2.6 | — |
| Comparative Example | | | |
| 1a | 35 | 3.0 | — |
| 1b | 80 | 0.9* | ± |
| 2 | 18 | 3.0 | ++ |

*fibrins contained in serum

TABLE 2

| Criteria for evaluating hemolysis Naked eye evaluation | |
|---|---|
| — | no hemolysis |
| ± | very mild hemolysis |
| + | mild hemolysis |
| ++ | moderate hemolysis |
| +++ | marked hemolysis |

What is claimed is:

1. A test tube assembly for serum separation which comprises a test tube and a layer formed on the inside wall of the test tube, the layer being formed of at least one compound selected from the group consisting of d-sesamin, l-sesamin, paulownin, d-asarinin, l-asarinin, 2α-paulownin, 6α-paulownin, pinoresinol, d-eudesmin, l-pinoresinol $\beta$-D-glucoside, l-pinoresinol, l-pinoresinol monomethyl ether $\beta$-D-glucoside, epimagnolin, lirioresinol-B, syringaresinol (dl), lirioresinon-B-dimethyl ether, phillyrin, magnolin, lirioresinol-A, 2α,6α-d-sesamin, d-diaeudesmin, lirioresinol-C dimethyl ether (d-diayangambin) and sesamolin.

2. A test tube assembly of claim 1 wherein the at least one compound is present in an amount ranging from 0.01 to 50 mg per ml of blood subject to separation in the assembly.

3. A test tube assembly for serum separation, which comprises a test tube and a carrier contained in the test tube, the carrier being coated with at least one compound selected from the group consisting of d-sesamin, l-sesamin, paulownin, d-asarinin, l-asarinin, 2α-paulownin, 6α-paulownin, pinoresinol, d-eudesmin, l-pinoresinol $\beta$-D-glucoside, l-pinoresinol, l-pinoresinol monomethyl ether $\beta$-D-glucoside, epimagnolin, lirioresinol-B, syringaresinol (dl), lirioresinon-B-dimethyl ether, phillyrin, magnolin, lirioresinol-A, 2α,6α-d-sesamin, d-diaeudesmin, lirioresinol-C dimethyl ether (d-diayangambin) and sesamolin.

4. A test tube assembly of claim 3 wherein the at least one compound is present in an amount ranging from 0.01 to 50 mg per ml of blood subject to separation in the assembly.

5. A test tube assembly of claim 3, wherein the carrier is selected from the group consisting of glass beads, glass fibers and powdered silica.

6. A test tube assembly of claim 1, wherein sealant for blood serum separation is contained in said test tube.

7. A test tube assembly of claim 3, wherein sealant for blood serum separation is contained in said test tube.

8. A test tube assembly of claim 5, wherein sealant for blood serum separation is contained in said test tube.

* * * * *